United States Patent
Oger et al.

(10) Patent No.: US 11,248,224 B2
(45) Date of Patent: Feb. 15, 2022

(54) **METHOD FOR OBTAINING A SMALL RNA-ENRICHED AQUEOUS EXTRACT OF *ANETHUM GRAVEOLENS***

(71) Applicant: ISP Investments LLC, Wilmington, DE (US)

(72) Inventors: Elodie Oger, Vallauris (FR); Jean-Marie Botto, Valbonne (FR)

(73) Assignee: ISP Investments LLC, Wilmington, DE (US)

( * ) Notice: Subject to any disclaimer, the term of this patent is extended or adjusted under 35 U.S.C. 154(b) by 238 days.

(21) Appl. No.: 16/612,365

(22) PCT Filed: Apr. 27, 2018

(86) PCT No.: PCT/EP2018/060926
§ 371 (c)(1),
(2) Date: Nov. 8, 2019

(87) PCT Pub. No.: WO2018/206322
PCT Pub. Date: Nov. 15, 2018

(65) Prior Publication Data
US 2021/0155921 A1    May 27, 2021

(30) Foreign Application Priority Data
May 12, 2017   (FR) ...................................... 1770486

(51) Int. Cl.
*C12N 5/10* (2006.01)
*A61K 8/9789* (2017.01)
(Continued)

(52) U.S. Cl.
CPC ........ *C12N 15/1017* (2013.01); *A61K 8/9789* (2017.08); *A61K 2800/805* (2013.01)

(58) Field of Classification Search
CPC ............ C12N 15/1017; C12N 15/1003; A61K 8/9789; A61K 2800/805; A61Q 19/08; A61Q 5/002; A61Q 19/007; A61Q 19/00
See application file for complete search history.

(56) References Cited

U.S. PATENT DOCUMENTS

| | | |
|---|---|---|
| 2010/0215785 A1 | 8/2010 | Kizoulis |
| 2010/0239510 A1 | 9/2010 | Ha |
| 2012/0308620 A1 | 12/2012 | Zadini |

FOREIGN PATENT DOCUMENTS

DE    102010027180 A1    5/2011

OTHER PUBLICATIONS

D5_XP002775075 Publication Date Oct. 12, 2015.
(Continued)

*Primary Examiner* — Trevor Love
(74) *Attorney, Agent, or Firm* — William J. Davis; Nathalie Tietcheu

(57) ABSTRACT

The invention relates to a method for obtaining an aqueous extract of *Anethum graveolens*, enriched with small RNAs having a maximum length of 150 nucleotides, from a plant material, said method comprising the following steps: a) aerial parts of dill is brought into contact with water; b) tetrasodium ethylenediaminetetraacetic acid (EDTA) is added at a pH of between 10.5 and 11; c) the pH of the mixture obtained in b) is then adjusted to a value of between 6 and 8; d) the mixture obtained in c) is purified; and e) the pH is checked and readjusted if necessary to a value of between 6 and 8. The invention also relates to an aqueous extract of *Anethum graveolens*, enriched with small RNAs having a maximum length of 150 nucleotides, obtained by the method.

6 Claims, 1 Drawing Sheet

(51) Int. Cl.
*C12N 15/10* (2006.01)
*A61Q 19/08* (2006.01)
*A61Q 5/00* (2006.01)
*A61Q 19/00* (2006.01)

(56) References Cited

OTHER PUBLICATIONS

Identification of RNA_Hydrolysis Products in NaOA-EDTA Extracts. References cited on the International Search report of PCT Application No. PCT/EP2018/060926 International Filing Date Apr. 17, 2018 and published under publication No. WO2018/206322 A1 on Nov. 15, 2018.

METHOD FOR OBTAINING A SMALL RNA-ENRICHED AQUEOUS EXTRACT OF ANETHUM GRAVEOLENS

CROSS-REFERENCE TO RELATED APPLICATIONS

This application is a U.S. National Phase filing under 35 U.S.C. § 371 of International Application No. PCT/EP2018/060926, filed Apr. 27, 2018, and published as WO 2018/26322 A1 on Nov. 15, 2018, which claims benefit of priority French Patent Application No. 1770486 filed May 12, 2017. The entire contents of each of the prior applications are incorporated herein by reference in their entirety.

The invention relates to a method for obtaining an aqueous extract of *Anethum graveolens* enriched with small RNAs having a maximum length of 150 nucleotides (nt), and also to the extracts obtained by the method, and the cosmetic compositions comprising such extracts and their cosmetic uses.

The family of the Apiaceae, also referred to as Umbelliferae, is formed by dicotyledonous plants and comprises almost 3,000 species spread across 420 genera, found in particular in the temperate regions of the world. This family also includes herbs, such as parsley, coriander, fennel. *Anethum graveolens* forms part of the family of the Apiaceae. Its species name assumes a number of synonyms, such as *Anethum sowa, Peucedanum graveolens* and *Peucedanum sowa* (Janeen et al; The Herb Society of America's Essential Guide to Dill. Kirtland, Ohio: The Herb Society of America, 2009). Dill (*Anethum graveolens*) is largely widespread throughout the world and is a species very rich in different families of molecules, such as essential oils, fatty acids, proteins, carbohydrates, furancoumarin, polyphenols, minerals and many more other biologically active molecules. It is used a lot in particular in traditional medicine. The genus name "*Anethum*" is derived from the Greek word "aneeson" or "aneeton" and means "strong smelling". This plant has a long and established history in numerous countries as a herb used in cooking and medicine. Its use is common in Ayurvedic medicine (traditional Indian medicine), primarily to combat abdominal discomfort and indigestion) (Jana et Shekhawat Shekhawat G S. Phytochemical Analysis and Antibacterial Screening of in vivo and invitro Extracts of Indian Medicinal Herb: *Anethum graveolens*. Res. J. Med. Plant. 2010a; 4(4):206-212. 2010; Janeen et al., The Herb Society of America's Essential Guide to Dill. Kirtland, Ohio: The Herb Society of America, 2009). In France and in many other West European countries, this plant is used in numerous traditional medicinal preparations due to its digestive and revitalising properties, which exist still today. The scientific literature describes in particular antimicrobial, anti-inflammatory and analgesic effects, protection of respiratory mucosae, and effects as a muscle relaxant.

Numerous extracts of dill seeds are described in the literature, in part with regard to use of the essential oils of the plant, whereas only a few studies have been performed on the extracts provided from the aerial parts of dill. Furthermore, the majority of the described extractions of dill are performed with organic solvents of the apolar kind, and only few extractions are performed with a polar solvent such as water. In addition, very few of these extracts are intended for cosmetic use.

In spite of the various anti-ageing cosmetic products available on the market for the treatment of skin, there remains a need for effective cosmetic compositions applied topically which have anti-ageing effects for the skin and hair and which use natural ingredients as active substance.

Products referred to as being "non-natural" and chemically synthesised may be perceived as being harmful to the environment and to people. By contrast, natural products are perceived as being superior to chemically synthesised products. Numerous natural products extracted from plants or herbs are known to contain antioxidant agents/free radicals which can neutralise the effects of free radical waste, such as polyphenols. Dill is a plant very rich in phenol compounds and other families of molecules recognised for their beneficial effects on the skin. In particular, the extraction method described in the invention makes it possible to enrich the final extract with RNAs of low molecular weight.

The protocols for extraction of ribonucleic acids (RNA, RNA of low molecular weight) described conventionally are tailored to laboratory practice, and therefore are performed on a small scale. They use solvents which are not considered to be cosmetic solvents (Zumbo, P. 2014 "Phenol-chloroform Extraction", 2014). In addition, these extraction and purification protocols only make it possible to obtain the purified nucleic acid fraction. This fraction of nucleic acids (RNA or DNA or small RNA) is devoid of any other molecule of interest, such as secondary metabolites, vitamins, sugars, peptides, etc., which could have beneficial effects for the skin and thus could be of cosmetic interest.

The first subject of the invention is a method for obtaining an aqueous extract of *Anethum graveolens* enriched with small RNAs having a maximum length of 150 nucleotides from a plant material, the method comprising the following steps:

a) solubilising aerial parts of dill in water;

b) adding tetrasodium ethylenediaminetetraacetic acid (EDTA) to the mixture obtained in a), the pH of the mixture being between 10.5 and 11;

c) then adjusting the pH of the mixture obtained in b) to a value between 6 and 8;

d) purifying the mixture obtained by separating the soluble material from the insoluble material in c) so as to recover an aqueous crude extract; and e) performing at least one filtration of the aqueous crude extract so as to obtain an aqueous extract enriched with small RNAs having a maximum length of 150 nucleotides, the pH of extract being checked, and, if necessary, readjusting the pH to a value between 6 and 8, preferably between 6 and 6.5.

Furthermore, a second subject of the invention is an aqueous extract of aerial parts of *Anethum graveolens* enriched with small RNAs having a maximum length of 150 nucleotides and comprising no DNA, obtained by the method according to the invention, characterised in that it comprises, by weight in relation to the total weight of the extract, from 5 to 30 g/kg of dry extract, 0.5 to 10 g/kg of protein fragments, 0.5 to 10 g/kg of sugars, 0.1 to 3 g/kg of amino acids, 50 to 2000 mg/kg of phenol compounds, and 10 to 100 mg/kg of RNA of low molecular weight having a maximum length of 150 nucleotides.

The invention also makes it possible to prepare a composition comprising, as active anti-ageing agent, an extract according to the invention, and a physiologically acceptable medium.

The invention and the advantages thereof will be better understood upon reading the following description and non-limiting embodiments with reference to FIG. 1 annexed hereto:

DESCRIPTION OF THE INVENTION

Figure 1:
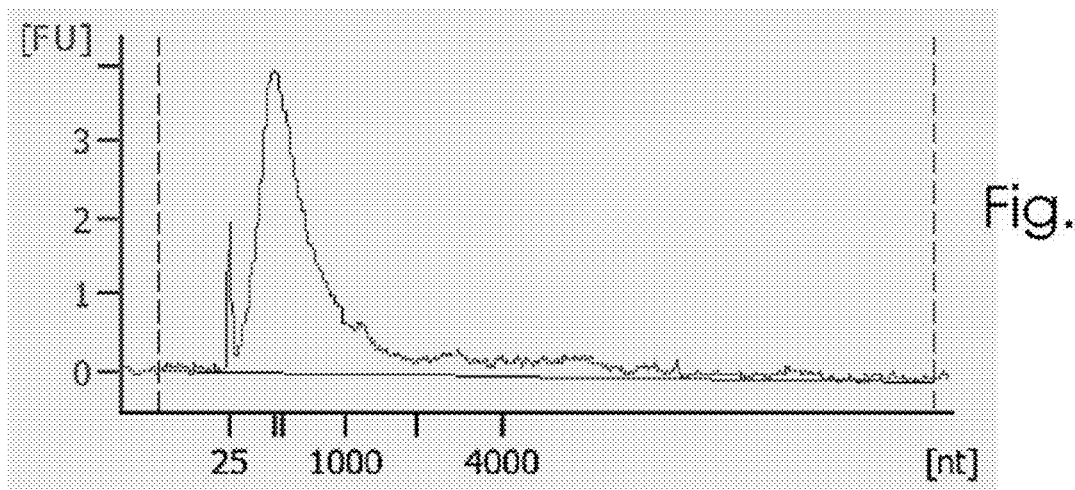
FIG. 1 is a graph depicting an analysis performed on a Bioanalyzer® showing the quantification of the RNAs of a dill extract obtained in accordance with example 1.

The invention relates to a method performed so as to obtain an aqueous extract enriched with small RNAs having a maximum length of 150 nucleotides from dried or fresh aerial parts of dill.

The term "aerial parts" means the leaves, stems and flowers of dill.

The seeds are not included in the "aerial parts" in the sense of the invention.

During the course of the description, the terms "dill" and "*Anethum graveolens*" will be used synonymously, with the same meaning.

The term "small RNA" or "RNA of low molecular weight" means non-coding RNAs (ribonucleic acids) of low molecular weight and having a maximum length of 150 nucleotides, such as all types of non-messenger small RNAs, either single-stranded and/or double-stranded, for example micro RNAs, interfering RNAs, introns, small nuclear RNAs, or any RNA fragment.

In a first step a) of the method according to the invention the plant material or ground, dried aerial parts of dill is placed in contact with water, preferably in a plant material/water ratio of 4 to 20% by weight/weight, more preferably in a ratio of from 5 to 10%, for example in a ratio of 5.7 or 10 by weight/weight.

The water used is a distilled demineralised water or a water rich in mineral salts and/or oligoelements, preferably a distilled water.

The aerial parts of dill is preferably in dry form.

The plant material is preferably ground before being placed in contact with water in step a). Grinding is a mechanical action which allows improved extraction. Mechanical grinding, followed by alkaline lysis in the presence of EDTA, promotes the complete de-structuring of the cell membrane and in particular the nuclear membrane.

Tetrasodium EDTA is then added in a step b) to the mixture obtained in a). The pH in this step is alkaline and must be adjusted, if necessary, to a value between 10.5 and 11 by adding sodium (NaOH). During step b) it is essential to hold the alkaline pH between 10.5 and 11. In fact, this pH level, combined with the action of the EDTA, causes the de-structuring of the cell membrane, including the nuclear membrane, lysis of the cells, and denaturation of the DNA (the 2 strands of the double helix are separated). The check of the pH in step b) shows that this remains alkaline and stabilises between 9 and 11.

The concentration of tetrasodium EDTA is preferably between 2 and 15 mM, and more preferably 10 mM.

This concentration of selected so as to optimise the extraction yield of RNAs of low molecular weight in the final extract. The tetrasodium EDTA will weaken and destroy the pectoceullosic membranes of the plant cells by sequestering by complexation of the divalent ions, such as the calcium ions which form ionic bridges between the molecules of pectins surrounding the microfibrils of cellulose. This has the result of promoting the release of the cell content during the extraction. The step of treatment by EDTA is essential to enrich the extract in RNA of low molecular weight.

The step of treatment by EDTA preferably lasts for at least 1 h, at a temperature between 20 and 80° C. During this step, the mixture obtained in a) was advantageously subjected to stirring.

In a step c) the pH of the mixture obtained in b) is then adjusted to a value between 6 and 8.

For example, the pH is adjusted by adding a solution of hydrochloric acid (HCl) or any acid capable of changing the pH and compatible with a cosmetic use, such as citric or lactic acid.

This step of acidification brings about the sudden renaturation of the DNA (re-pairing of the strands of the duplex). Nevertheless, chromosomal DNA, which is very long, does not completely re-pair and forms insoluble tangles. By contrast, small RNAs, which are much shorter, remain in solution. The DNA and the small RNAs are then separated into two separate phases: a solid phase containing, amongst other things, chromosomal DNA, and a liquid phase containing, amongst other things, small RNAs.

In a step d) the mixture obtained in c) is purified so as to eliminate the plant material and recover a crude aqueous extract. Any method known to a person skilled in the art could be used. The mixture obtained in c) is preferably centrifuged at low speed, for example for at least 10 min at 4000 g, so as to sediment the residual plant material in the pellet and recover a crude aqueous extract in the supernatant.

In a step d) the pH is checked and readjusted to a value between 6 and 8. The pH is preferably readjusted to a value between 6 and 6.5, even more preferably to 6.5. The pH is readjusted by the addition of a solution of hydrochloric acid (HCl) or sodium (NaOH).

In fact, a pH lower than 6 may drive precipitation of nucleic acids in general, and therefore that of RNAs of low molecular weight having a maximum length of 150 nucleotides.

The step of adjusting the pH in step d) of the method according to the invention is a step that is indispensable for optimal extraction of RNAs of low molecular weight.

The readjustment of the pH in step d) is advantageously preceded by at least one filtration of the crude aqueous extract obtained in d). Successive filtrations will preferably be performed by lowering the filtration threshold by 50 to 20 μm to 0.4; 0.3; 0.2; or 0.1 μm.

The second subject of the invention is an aqueous extract of dill enriched with small RNAs having a maximum length of 150 nucleotides of the invention, obtained by the method described above.

This extract does not contain DNA (deoxyribonucleic acid).

Such an aqueous extract enriched with small RNAs having a maximum length of 150 nucleotides comprises, prior to dilution, by weight in relation to the total weight of the extract, 10 to 30 g/kg of dry weight extract, 2 to 10 g/kg of protein fragments, 2 to 10 g/kg of sugars, 0.2 to 3 g/kg of amino acids, 100 to 2000 mg/kg of phenol compounds, and 10 to 100 mg/kg of RNA of low molecular weight having a maximum length of 150 nucleotides. The extract thus obtained is considered to be concentrated. It may then be diluted in a physiologically acceptable solvent for cosmetic use, such that the concentration of the extract is then adjusted to a particular dry extract weight of interest.

Illustrative and non-limiting examples of physiologically acceptable solvents include water, glycerol, ethanol, propanediol and is natural version called Zemea® derived from corn, butylene glycol, dipropylene glycol, ethoxylated or propoxylated diglycols, cyclic polyols, or any mixture of these solvents.

The extract obtained by the method according to the invention is preferably diluted in a solvent such as 30% glycerol and water After dilution, the extract comprises 5-15 g/kg of dry extract, from 50 to 1000 mg/kg of polyphenols 0.5-10 g/kg of protein fragments, 0.5-10 g/kg of sugars, from 0.1 to 1 g/kg of amino acids, and 10-100 mg/kg of small RNAs having a maximum length of 150 nucleotides.

Preferred embodiments of the method according to the invention will be described hereinafter by way of illustration.

Example 1: Preparation of a Small RNA-Enriched Extract of Dill (*Anethum graveolens*) from the Family of Apiaceae A aqueous extract enriched with RNA of low molecular weight (having a maximum length of 150 nucleotides) is obtained from dill (*Anethum graveolens*) from the family of the Apiaceae.

In a first step, 5% of dried aerial parts of dill in the form of a powder are placed in distilled water, and 10 mM of tetrasodium EDTA are added, that is to say 50 g of dried dill powder in 950 g of distilled water and 3.8 g of tetrasodium EDTA. The pH in this step should be alkaline and comprised between 10.5 and 11 for optimal enrichment of the extract with RNA of low molecular weight.

The mixture is then heated for 2 h at 55° C. with stirring.

The mixture is then centrifuged for 10 min at 4000 g in order to remove the solid matter.

At the end of this step the pH is checked, before any dilution, so as to adjust it, if necessary, to between 6 and 6.5 and preserve the small RNAs of the extract.

Sequential filtrations over filters of decreasing porosity are then performed in order to refine the plant extract, up to a sterilising filtration at 0.2 μm.

Example 2: Characterisation of the Extract of Dill from Example 1

Generally, what is obtained is a light green-coloured aqueous extract of dill, containing from 10 to 30 g/kg of dry weight extract, 2 to 10 g/kg of protein fragments, 2 to 10 g/kg of sugars 0.1 to 3 g/kg of amino acids, 300 to 750 mg/kg of phenol compounds, and 10 to 100 mg/kg of RNA of low molecular weight having a maximum length of 150 nucleotides.

Nevertheless, for aerial parts of dill of the *Anethum graveolens* species, the obtained extracts may vary considerably depending on factors such as the harvest area, the harvest year, the season, the climatic conditions, etc.

In the extraction of example 1, an aqueous extract containing 12 g/kg of dry weight extract was obtained.

The physico-chemical analysis shows that this extract has a concentration of 2.55 g/kg of protein fragments, 3 g/kg of sugars, 340 g/kg of amino acids, 650 mg/kg of phenol compounds, and 50 mg/kg of RNA of low molecular weight having a maximum length of 150 nucleotides. The extract is then diluted with a cosmetic solvent in particular with 30% glycerol or butylene glycol or propanediol. After dilution the extract has a concentration of 1.7 g/kg of protein fragments, 2 g/kg of sugars, 240 g/kg of amino acids, 455 mg/kg of phenol compounds, and 35 mg/kg of RNA of low molecular weight having a maximum length of 150 nucleotides.

Methods used in the spectrophotometry assay to determine the quantity of different compound in the dill extract:

The total content of proteins in the dill extract was determined by a Lowry protein assay (Lowry et al, 1951). The absorption of the sample is read on the spectrophotometer at 550 nm. The content of proteins is determined with the aid of BSA standard curve.

The content of amino acids in the extract was determined on the basis of a protocol published by Moore et al (1948), the content of free amino acids was assessed by the formation of a coloured complex following the breakdown of the amine and carboxylic functionalities by the reagent ninhydrin. The absorption of the complex is read on the spectrophotometer at 570 nm. The total content of amino acids is determined in relation to an amino acid pool as standard.

The total content of sugars in the extract was determined by adaptation of the dosage described by Dubois et al. (1956) (Dubois et al., "Colorimetric method for determination of sugars and related substances, Anal. Chem., 1956, 28 (3), 350-356). This analysis consists of the dissolution of the first material in concentrated sulfuric acid, then reaction with phenol to form a coloured complex. The absorption of the complex is read on the spectrophotometer at 490 nm. The content of sugar is determined with the aid of a glucose standard curve.

The content of polyphenols in the extract was determined with the aid of the Folin-Ciocalteu assay (Singleton et al., "Analysis of total phenols and other oxidation substrates and antioxidants by means of Folin-Ciocalteu reagent, Methods Enzymol. 1999, 299: 152). The compounds of the polyphenol type in the sample react with the Folin-Ciocalteu reagent; the oxidation of the reagent gives a blue colour. The absorption of the sample is read on the spectrophotometer at 760 nm. The content was expressed in equivalents of gallic acid with the aid of a gallic acid standard curve.

The RNAs of low molecular weight are quantified by means of a Bioanalyzer® (Agilent), which makes it possible to perform miniaturised electrophoresis thanks to electronic chips specific for the analysis of nucleic acids, such as the analysis of RNAs of low molecular weight. This makes it possible to determine the size and the concentration contained in an extract on the basis of a few microlitres. The result is presented in the form of a graph with an arbitrary unit of fluorescence on the ordinate (FU) and the number of nucleotides on the abscissa (nt). An internal marker is added to each analysis (peak at 25 nt in FIG. 1), and serves as an internal control to validate good execution of the analysis.

Example 3: Study of the Effect of the Final pH in the Preparation of Extracts of Dill (*Anethum graveolens*) so as to Obtain an Extract of Dill Devoid of Small RNAs The extraction process was performed under the same working conditions as example 1, to enrich an extract with RNA of low molecular weight, apart from the final step of adjustment of the pH.

This extraction process is performed with a step of treatment by tetrasodium EDTA, but with a final adjustment of the extract at an acidic pH between 4 and 4.5 instead of a pH between 6 and 8.

Figure 2:
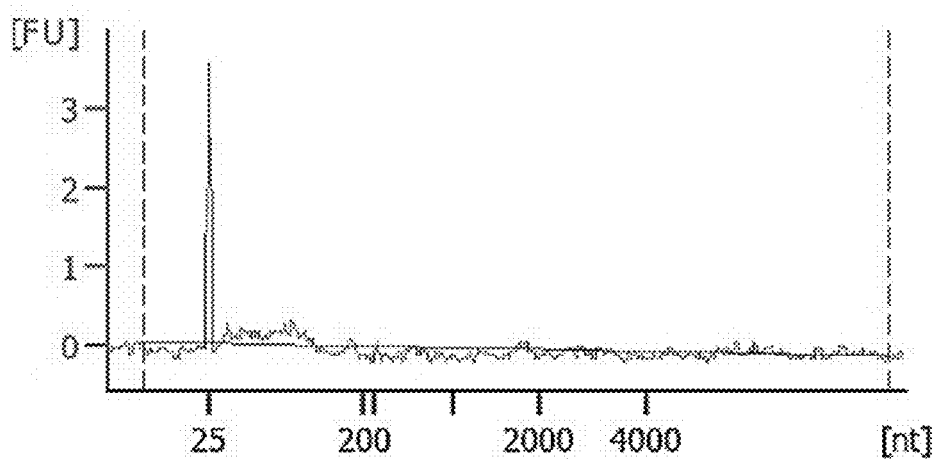
FIG. 2 shows a graph depicting an analysis performed on a Bioanalyzer® showing the quantification of the RNAs of a dill extract obtained after a step of precipitation of small RNA according to example 2.

This leads to the precipitation of RNAs of low molecular weight, these results being confirmed by the analysis of the Bioanalyzer®, which gives a concentration of RNA of low molecular weight of zero (as shown in FIG. 2).

Example 4: Provision of a Conventional Extract Obtained by Maceration of Dill (*Anethum graveolens*). Determination of the Role of a Step of Treatment by ETA for Implementation of a Method for the Extraction of Small RNAs With the aim of demonstrating the role of a step of treatment by EDTA during the extraction of RNAs of low molecular weight, an extract of dill (*Anethum graveolens*) was also obtained by modifying certain essential steps of the method according to the invention, preventing enrichment of the extract with RNA of low molecular weight.

In a first step, 5% dill are ground, the water is added, that is to say 50 g of dill in 950 g of distilled water.

The pH is measured and is 5.5; the mixture is stirred for 1 h at 55° C.

Then, the extract is centrifuged for 10 min at 4000 g to remove the solid matter.

Sequential filtrations are then performed over filters of decreasing porosity size between 50 and 20 μm, then to a porosity of from 0.4 to 0.3 μm.

A light green-coloured aqueous extract containing 13 g/kg of dry weight extract, containing 3.3 g/kg of protein fragments, 2.2 g/kg of sugars, 380 mg/kg of amino acids, and 410 mg/kg of phenol compounds is then obtained.

The extract is then diluted to 8 g/Kg of dry weight, solely by addition of water.

Figure 3:
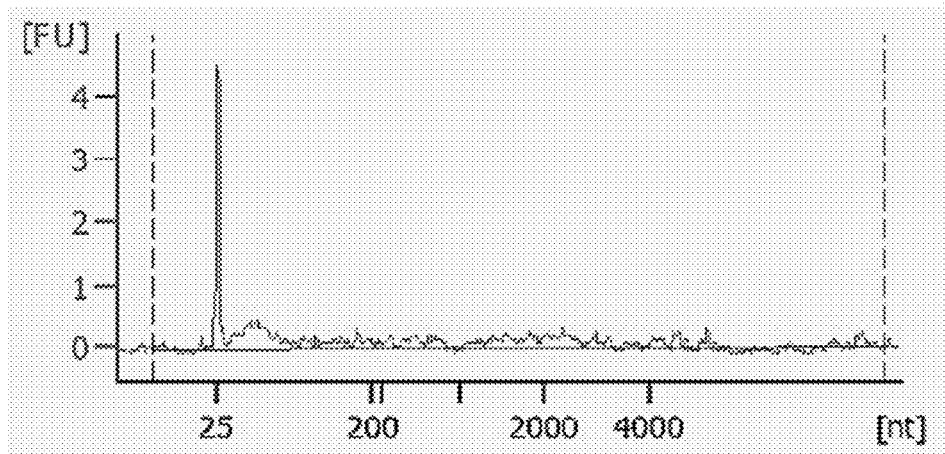
FIG. 3 is a graph depicting an analysis performed on a Bioanalyzer® showing the quantification of the RNAs of a dill extract obtained by conventional extraction in accordance with example 3.

The physico-chemical analysis shows that, after dilution, the plant extract has a concentration of protein fragments of 2.8 g/kg, and of sugars of 1.7 g/kg, of amino acids of 240 mg/kg, and of phenol compounds of 280 mg/kg. Under these extraction conditions, which are said to be conventional (absence of treatment by EDTA), the analysis of the Bioanalyzer® reveals that the concentration of RNA of low molecular weight is zero for this extract (as shown in FIG. 3). This result confirms that an extract obtained by an extraction process in the absence of treatment by EDTA (at alkaline pH) does not contain RNA of low molecular weight. The step of treatment by EDTA is essential to obtain an extract rich in RNA of low molecular weight according to the invention.

According to another aspect of the invention, the aqueous extracts enriched with small RNAs obtained in accordance with the invention are advantageously used in the preparation of cosmetic compositions comprising, as active substance, an extract of small RNA of this kind according to the invention, and a physiologically acceptable medium.

The term "effective amount" means the minimum amount of extract according to the invention which is necessary to obtain the activity of the extract, in particular the cosmetic activity and more particularly to improve the akin, fight against the signs of skin ageing, or to improve the hydration of the skin, without this amount being toxic.

The extract of small RNAs according to the invention is advantageously used, preferably diluted, in a cosmetic solvent, at a dry weight between 5 and 15 g/kg.

The extract of small RNAs according to the invention is advantageously present in the composition at a concentration of from 0.1 to 5% by weight relative to the total weight of the composition.

A physiologically acceptable medium denoted a vehicle suitable for contacting the outer surfaces of the skin or mucosae, without toxicity, irritation, induced allergic reaction and the like or intolerance reaction, and dosed to a sensible advantage/risk ratio.

The composition usable in accordance with the invention could be applied by any suitable route, in particular orally, or topically externally, and the formulation of the compositions will be adapted by a person skilled in the art.

The compositions according to the invention are preferably present in a form suitable for topical application. These compositions therefore must contain a physiologically acceptable medium, that is to say one that is compatible with the skin and appendages, with no risk of discomfort at the time of their application, and encompass all suitable cosmetic forms.

Topical application denotes the fact of applying or spreading the aqueous extract enriched with small RNAs according to the invention, and more particularly a composition containing same, on the skin surface or a mucosa.

The term "skin" denotes the skin of the face, in particular the contour of the eyes and the mouth, the nose, the forehead, the neck, the hands, but also the skin of the entire body.

The compositions for implementing the invention could be presented in particular in the form of an aqueous, hydro-alcoholic or oily solution, an oil-in-water emulsion, or water-in-oil emulsion. They could also be presented in the form of suspensions or even powders, suitable for application to the skin, mucosae, lips, and/or hair.

These compositions may be fluid to a greater or lesser extent and may also have the appearance of a cream, a lotion, a milk, a serum, a pomade, a gel, a paste or a foam. They may also be presented in solid form, as a stick, or may be applied to the skin in aerosol form.

Examples of a physiologically acceptable medium commonly used in the envisaged field of application include the additives necessary for the formulation, such as solvents, thickeners, diluents, antioxidants, colourants, sun filters, self-tanning agents, pigments, fillers, preservatives, perfumes, odour absorbers, essential oils, vitamins, essential fatty acids, surfactants, filmogenic polymers, etc.

In any case, a person skilled in the art will ensure that these additives as well as their proportions are selected to as not to compromise the advantageous properties sought of the composition according to the invention. These additives may correspond, for example, to 0.01 to 20% of the total weight of the composition. When the composition according to the invention is an emulsion, the fatty phase may represent from 5 to 80% by weight, and preferably from 5 to 50% by weight in relation to the total weight of the composition. The emulsifiers and co-emulsifiers used in the composition are selected from those used conventionally in the field in question. For example, they can be used in a proportion ranging from 0.3 to 30% by weight in relation to the total weight of the composition.

In accordance with a further advantageous embodiment of the invention, the aqueous extract enriched with small RNAs according to the invention can be encapsulated or included in a cosmetic vector, such as liposomes or any other nanocapsule or microcapsule used in the field of cosmetics or adsorbed on powdered organic polymers or mineral supports, such as talcs and bentonites.

The composition according to the invention advantageously may comprise, in addition to the active substance according to the invention, at least one other active substance having cosmetic effects similar and/or complementary to those of the invention. In accordance with the invention this active substance is defined as an "additional active substance".

For example, the additional active substance(s) may be selected from: anti-ageing, firming, brightening, hydrating, draining, microcirculation-promoting, exfoliating, desquamating, extracellular matrix-stimulating, energy metabolism-activating, antibacterial, anti-fungal, soothing, anti-radical, anti-UV, anti-acne, anti-inflammatory and anaesthetic substances, substances inducing a sensation of heat or a sensation of freshness, and slimming substances.

Such additional active substances can be selected from the groups comprising:
- vitamin A and in particular retinoic acid, retinol, retinol propionate, retinol palmitate;
- vitamin B3 and more particularly niacinamide, tocopherol nicotinate;
- vitamin B5, vitamin B6, vitamin B12, panthenol;
- vitamin C, in particular ascorbic acid, ascorbyl glucoside, ascorbyl tetrapalmitate, magnesium and sodium ascorbyl phosphate;
- vitamins E, F, H, K, PP, coenzyme Q10;
- inhibitors of metalloproteinase, or an activator of TIMPs;
- DHEA, its precursors and derivatives;
- amino acids such as arginine, ornithine, hydroxyproline, hydroxyproline dipalmitate, palmitoylglycine, hydroxylysine, methionine and derivatives thereof, N-acyl amino acid compounds;
- natural or synthetic peptides, including the di-, tri-, tetra-, penta- and hexapeptides and their lipophilic and isomeric derivatives and their derivatives complexed with other species, such as a metal ion (for example copper, zinc, manganese, magnesium, and others). Examples include the peptides known commercially by the name MATRIXYL®, ARGIRELINE®, CHRONOGEN™, LAMINIXYL IS™, PEPTIDE Q10™, COLLAXYL™ (brevet FR2827170, ASHLAND®), PEPTIDE VINCI 01™ (patent FR2837098, ASHLAND®), PEPTIDE VINCI 02™ (patent FR2841781, ASHLAND®), ATPeptide™ (patent FR2846883, ASHLAND®) or also the synthetic peptide of sequence Arg-Gly-Ser-NH$_2$, sold under the name ATPeptide™ by ASHLAND®;
- the extract of *Artemia salina*, sold under the name GP4G™ (FR2817748, ASHLAND®);
- plant peptide extracts, such as extracts of flax (Lipigenine™, patent FR2956818, ASHLAND®), extracts of soybean, spelt, vine, rape, flax, rice, corn, pea;
- yeast extracts, for example Dynagen™, (patent FR2951946, ASHLAND®) or Actopontine™ (patent FR2944526, ASHLAND®);
- dehydroacetic acid (DHA);
- phytosterols of synthetic or natural origin;
- salicylic acid and derivatives thereof, alpha- and beta-hydroxy acids, silanols;
- amino sugars, glucosamine, D-glucosamine, N-acetyl glucosamine, N-acetyl-D-glucosamine, mannosamine, N-acetyl mannosamine, galactosamine, N-acetyl galactosamine;
- extracts of polyphenols, isoflavones, flavonoids, such as extracts of grape, extracts of pine, extracts of olive;
- lipids, such as the ceramides or phospholipids, oils of animal origin, such as squalene or squalane; plant oils, such as sweet almond oil, coconut oil, castor oil, jojoba, oil, olive oil, rape oil, peanut oil, sunflower oil, wheat germ oil, maize germ oil, soybean oil, cotton oil, alfalfa oil, poppy oil, pumpkin oil, evening primrose oil, millet oil, barley oil, rye oil, safflower oil, passiflora oil, hazelnut oil, palm oil, apricot kernel oil, avocado oil, calendula oil; ethoxylated plant oils, shea butter;
- all UV screens and sun filters;
- cyclic AMP and derivatives thereof, substances that are activators of the adenylate cyclase enzyme and substances that are inhibitors of the phosphodiesterase enzyme, the extract of *Centella asiatica*, asiaticoside and asiatic acid, methylxanthines, theine, caffeine and derivatives thereof, theophylline, theobromine, forskolin, esculin and esculosid, ACE inhibitors, the peptide Val-Trp, inhibitors of neuropeptide Y, enkephalin, extract of *Ginkgo biloba*, extract of dioscorea, rutin, extract of yerba mate, extract of guarana, oligosaccharides, polysaccharides, carnitine, extract of ivy, extract of fucus, hydrolysed extract of *Prunella vulgaris*, hydrolysed extract of *Celosia cristata*, extract of *Anogeissus leiocarpus*, extract of leaves of *Manihot utilissima*, palmitoyl carnitine, carnosine, taurine, extract of elder, extracts of seaweed, such as the extract of *Palmaria Palmata*.

By way of illustration, examples of formulations of a cosmetic composition containing an aqueous extract enriched with small RNAs having a maximum length of 150 nucleotides, obtained in accordance with the invention will be described hereinafter:

Example 5: Eye Contour Balm

| Ingredients (trade name) | INCI | % w/w |
|---|---|---|
| Phase A | | |
| Purified water | Aqua | Qsp 100 |
| Tetrasodium EDTA | Tetrasodium EDTA | 0.01 |
| Phase B | | |
| RapiThix ™ A-100 polymer | Sodium Polyacrylate | 1.80 |
| Phase C | | |
| Cegesoft VP | Vegetable oil (and) Hydrogenated vegetable oil (and) *Euphorbia Cerifera* (*Candelilla*) Wax | 3.00 |
| Si-Tec ™ GF 3096 silicone | Dimethicone (and) Dimethiconol | 10.00 |
| Phase D | | |
| DC 9701 Cosmetic Powder | Dimethicone/Vinyl Dimethicone Crosspolymer (and) Silica | 1.00 |
| Phase E | | |
| Optiphen ™ preservative | Phenoxyethanol (and) Caprylyl Glycol | 0.50 |
| Phase F | | |
| Extract according to example 1 | Water/Aqua (and) Glycerin (and) Peucedanum Graveolens (Dill) extract | 1.00 |
| Zemea ® | Propanediol | 5.00 |
| Timiron Splendid Violet | CI 77891 (Titanium Dioxide) (and) Mica (and) Silica | 1.00 |

Preparation Process:
1. Homogenise phase A in the main vessel until it is clear;
2. At 25° C., sprinkle into phase B and homogenise for 10 minutes to homogeneity;
3. At 25° C., prepare phase C in a separate beaker, mix to homogeneity. Sprinkle into phase D and mix well to homogeneity;

4. At 25° C., add phase C+D to the main vessel and mix to homogeneity;
5. At 25° C., add phase E to the main vessel and mix to homogeneity;
6. At 25° C., pre-mix phase F, add it to the main vessel, and mix to homogeneity;
7. Stop at 25° C.

The composition is thus present in the form of a pearly violet cream gel, with a pH between 5.70 and 6.20 and a viscosity (D0) of 80000-130000 cps (Brookfield RVT/Spindle C/5 RPM/1 minute/25° C.)

Example 6: Rich Cream

| Ingredients (trade name) | INCI | % w/w |
|---|---|---|
| Phase A | | |
| Purified water | Aqua | Qsp |
| Optiphen ™ Plus preservative | Phenoxyethanol (and) Caprylyl Glycol (and) Sorbic Acid | 1.50 |
| Phase B | | |
| Stabileze ™ QM polymer | PVM/MA Decadiene Crosspolymer | 0.15 |
| Phase C | | |
| ProLipid ™ 141 lamellar gel | Glyceryl Stearate (and) Behenyl Alcohol (and) Palmitic Acid (and) Stearic Acid (and) Lecithin (and) Lauryl Alcohol (and) Myristyl Alcohol (and) Cetyl Alcohol | 5.00 |
| Ceraphyl ™ 494 ester | Isocetyl Stearate | 4.00 |
| Ceraphyl ™ SLK ester | Isodecyl Neopentanoate | 4.00 |
| DC 580 Wax | Stearoxytrimethylsilane (and) Stearyl Alcohol | 2.00 |
| Emulsynt ™ GDL ester | Glyceryl Dilaurate | 3.00 |
| Phase D | | |
| Gransil DM-5 | Dimethicone (and) Polysilicone-11 | 3.00 |
| Phase E | | |
| Sodium Hydroxide | Sodium Hydroxide | 0.04 |
| Purified water | Aqua | 0.50 |
| Phase F | | |
| PF precious wood | Perfume/Fragrance | 0.30 |
| Unipure* Red LC 381 ADT-C | CI 77491 (Iron oxides) (and) Isopropyl Titanium Triisostearate (and) Bis-Hydroxyethoxypropyl Dimethicone (and) PEG-2-Soyamine (and) Isophorone Diisocyanate | 0.03 |
| Phase G | | |
| Extract according to example 1 | Water/Aqua (and) Glycerin (and) Peucedanum Graveolens (Dill) extract | 3.00 |
| Ronaflair Balance Gold | CI 77891 (Titanium Dioxide) (and) Mica (and) Tin Oxide | 0.30 |
| Covabead Velvet 10 | Polymethyl Methacrylate | 1.00 |
| Ronaflair Balance Red | CI 77891 (Titanium Dioxide) (and) Mica (and) Tin Oxide | 1.20 |
| Phase H | | |
| Purified water | Aqua | 15.00 |
| Natrosol ™ Plus 330 CS | Cetyl Hydroxyethylcellulose | 0.50 |

Preparation Process:
1. Homogenise phase A in the main vessel and start to heat to 75-80° C.;
2. At 30° C., sprinkle into phase B and homogenise whilst heating;
3. In a separate beaker, prepare phase C, heat to 75-80° C. to homogeneity;
4. At 75° C., add phase C to the main vessel and homogenise for 10 minutes;
5. Leave to cool and add phase D at 65° C. Mix well to homogenise for 10 minutes;
6. Pre-mix phase E before adding to the main vessel;
7. Add phase E at 60° C. Mix well to homogenise for 10 minutes;
8. At 35° C., pre-mix phase F before adding and mixing well;
9. Pre-mix phase G before adding to the main vessel;
10. Add phase G at 35° C. Mix well to homogenise;
11. In a separate beaker, prepare phase H: sprinkle Natrosol™ into water at ambient temperature and homogenise whilst heating to 60° C.;
12. Add phase H at 30° C. Mix well to homogenise;
13. Stop at 25° C.

The composition is thus present in the form of a pink buttery cream, with a pH between 4.90 and 5.40 and a viscosity (D0) of 160000-210000 cps (Brookfield RVT/Spindle D/5 RPM/1 minute/25° C.)

Example 7: Face Serum

| Ingredients (trade name) | INCI | % w/w |
|---|---|---|
| Phase A | | |
| Purified water | Aqua | Qsp 100 |
| Propylene Glycol | Propylene Glycol | 35.10 |
| SD Alcohol 40B Absolute | Alcohol | 10.00 |
| Butylene Glycol | Butylene Glycol | 5.00 |
| Disodium EDTA | Disodium EDTA | 0.10 |
| Phase B | | |
| Flexithix ™ polymer | PVP | 2.00 |
| Phase C | | |
| Xanthan gum | Xanthan Gum | 0.25 |
| Phase D | | |
| Rapithix ™ A-60 polymer | Sodium Polyacrylate (and) Hydrogenated Polydecene (and) Trideceth-6 | 1.00 |
| Rokonsal ™/LiquaPar ™ MEP preservative | Phenoxyethanol (and) Methylparaben (and) Ethylparaben (and) Propylparaben | 0.70 |
| Phase E | | |
| Extract according to example 1 | Water/Aqua (and) Glycerol (and) Peucedanum Graveolens (Dill) extract | 5.00 |
| Phase F | | |
| Cyclopentasiloxane DM 350 | Cyclopentasiloxane | 6.00 |
| | Dimethicone | 3.00 |
| Gransil* DMCM-5 | Dimethicone (and) Cyclopentasiloxane (and) Polysilicone-11 | 1.50 |
| KSP* 100 | Vinyl Dimethicone/Methicone Silsesquioxane Crosspolymer | 1.00 |
| Phase G | | |
| Unicert* Yellow 08006-J | Water/Aqua (and) CI 15985 (Yellow 6) | 0.60 |

Preparation Process:
1. Weigh the ingredients of phase A into a beaker at ambient temperature and mix. Sprinkle phase B in, and homogenise;
2. At ambient temperature, sprinkle into phase C and continue to homogenise the mixture;
3. At ambient temperature, add phase D to phase ABC and continue to homogenise;
4. At ambient temperature, add phase E and homogenise;

5. At ambient temperature, add phase F and homogenise the mixture;

6. At ambient temperature, add phase G and mix to homogeneity;

7. Stop at 25° C.

The composition is thus present in the form of a smooth, creamy, yellow, translucent gel, with a pH between 6.30 and 7.10 and a viscosity (D0) of 10000-15000 cps (Brookfield RVT/Spindle B/5 RPM/1 minute/25° C.)

Example 8: Anti-Ageing Mask

| Ingredients (trade name) | INCI | % w/w |
|---|---|---|
| Phase A | | |
| Purified water | Aqua | Qsp 100 |
| Tetrasodium EDTA | Tetrasodium EDTA | 0.05 |
| Phase B | | |
| N-Hance ™ HP40S guar | Hydroxypropyl Guar | 0.10 |
| Phase C | | |
| Lubrajel ™ DV Free hydrogel | Glycerin (and) Glyceryl Acrylate/Acrylic Acid Copolymer | 6.00 |
| Phase D | | |
| Si-Tec ™ GF 3096 silicone | Dimethicone (and) Dimethiconol | 12.00 |
| RapiThix ™ A-60 polymer | Sodium Polyacrylate (and) Hydrogenated Polydecene (and) Trideceth-6 | 2.40 |
| Phase E | | |
| Optiphen ™ Plus preservative | Phenoxyethanol (and) Caprylyl Glycol (and) Sorbic Acid | 1.50 |
| Phase F | | |
| Surfin* 96 | Alcohol Denat. | 3.50 |
| PF Cucumber & Aloe | Perfume/Fragrance | 0.50 |
| Phase G | | |
| Extract according to example 1 | Water/Aqua (and) Glycerol (and) Peucedanum Graveolens (Dill) extract | 1.00 |
| Achromaxyl ™ ISR biofunctional | Water/Aqua (and) Glycerin (and) Hydrolyzed Brassica Napus Seedcake Extract | 3.00 |
| Xirona Carribean Blue | Mica (and) CI 77891 (Titanium Dioxide) (and) Silica (and) Tin Oxide | 1.00 |

Preparation Process:

1. At 25° C., homogenise phase A in the main vessel;

2. At 25° C., sprinkle into phase B and mix well to homogeneity;

3. At 25° C., add phase C and mix well to homogeneity;

4. Pre-mix phase D in a separate beaker and add to the main vessel at 25° C.;

5. At 25° C., add phase E to the main vessel and mix well;

6. Pre-mix phase F and add it slowly. Mix well to homogeneity;

7. Pre-mix phase G in a separate beaker and add to the main vessel to homogeneity;

8. Stop at 25° C.

The composition is thus present in the form of a creamy gel with a shimmery green effect, with a pH between 5.30 and 5.80 and a viscosity (D0) of 70000-100000 cps (Brookfield RVT/Spindle C/5 RPM/1 minute/25° C.)

Example 9: Serum

| Ingredients (trade name) | INCI | % w/w |
|---|---|---|
| Phase A | | |
| Demineralised water | Aqua | 87.40 |
| Sodium Hyaluronate | Sodium Hyaluronate | 0.20 |
| RapiThix ™ A-60 polymer | Sodium Polyacrylate (and) Hydrogenated Polydecene (and) Trideceth-6 | 0.40 |
| Lubrajel ™ DV hydrogel | Glycerin (and) Glyceryl Acrylate/Acrylic Acid Copolymer (and) Propylene Glycol | 6.00 |
| Lubrajel ™ Oil hydrogel | Glycerin (and) Glyceryl Acrylate/Acrylic Acid Copolymer (and) Propylene Glycol (and) PVM/MA Copolymer | 1.00 |
| Wacker-Belsil* DM 100 | Dimethicone | 2.00 |
| Cyclopentasiloxane NF | Cyclopentasiloxane | 0.50 |
| Extract according to example 1 | Water/Aqua (and) Glycerol (and) Peucedanum Graveolens (Dill) extract | 1.00 |
| Optiphen ™ preservative | Phenoxyethanol (and) Caprylyl Glycol | 1.50 |

Preparation Process:

1. Add water to the main vessel and start to mix using a hi-lo propeller paddle;

2. Add the rest of the ingredients one after the other, mixing between each addition.

The composition is thus present in the form of a smooth semi-opaque serum with a pH between 5.75 and 6.25 and a viscosity (D0) of 1,100-1,400 cps (Brookfield RVT/spindle 3/20 rpm/25° C./1 minute).

The cosmetic compositions described above can be used to improve the appearance of the skin, fight against the signs of skin ageing, or to improve skin hydration.

The expression "improve the appearance of the skin" means that the skin texture appears smoother, the luminosity of the skin is more intense, and the complexion is more even.

The expression "signs of skin ageing" means any changes to the external appearance of the skin caused by ageing, such as wrinkles and lines, cracks, bags beneath the eyes, shadows, sagging, loss of elasticity, firmness and/or tone of the skin, but also any changes within the skin itself which are not manifested systematically by a changed outer appearance, such as a thinning of the skin, or any internal degradation of the skin caused by environmental stress, such as pollution and UV rays.

The term "improve skin hydration" means any improvements to changes in the outer appearance of the skin caused by dehydration, for example dryness, tightness and discomfort.

The invention claimed is:

1. A method for obtaining an aqueous extract of the aerial parts of *Anethum graveolens* having a maximum length of 150 nucleotides from a plant material, the method comprising the following steps:
   a) bringing aerial parts of *Anethum graveolens* into contact with water;
   b) adding tetrasodium ethylenediaminetetraacetic acid (EDTA) to the mixture obtained in a), the pH of the mixture being between 10.5 and 11;
   c) then adjusting the pH of the mixture obtained in b) to a value between 6 and 8;
   d) purifying the mixture obtained in c) so as to eliminate the residual solid plant material and obtain a purified crude aqueous extract; and e) checking the pH and readjusting it, if necessary, to a value between 6 and 8, preferably between 6 and 6.5.

2. The method according to claim 1, characterised in that, in step a), the plant material previously dried and then ground is brought into contact with water in a ratio of plant material/water between 4 and 20% (weight/weight).

3. The method according to claim 1, characterised in that the step b) of treatment by tetrasodium ethylenediaminetetraacetic acid (EDTA) is performed under stirring for a period of at least 1 h and at a temperature between 20 and 80° C.

4. The method according to claim 1, characterised in that, in step d), the mixture obtained in c) is centrifuged.

5. The method according to claim 1, characterised in that step e) is preceded by at least one filtration of the crude aqueous extract obtained in d) and preferably by successive filtrations of the crude aqueous extract by lowering the filtration threshold by 20-50 μm to 0.1-0.30 μm.

6. The method according to claim 1, characterised in that the concentration of tetrasodium EDTA is between 2 and 15 mM, preferably is 10 mM.

* * * * *